United States Patent
Nagasaka et al.

(10) Patent No.: US 9,684,041 B2
(45) Date of Patent: Jun. 20, 2017

(54) PRODUCTION METHOD OF GAS CELL, AND GAS CELL

(71) Applicant: Seiko Epson Corporation, Tokyo (JP)

(72) Inventors: Kimio Nagasaka, Hokuto (JP); Kazumichi Kikuhara, Kawasaki (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/846,494

(22) Filed: Sep. 4, 2015

(65) Prior Publication Data

US 2015/0377984 A1 Dec. 31, 2015

Related U.S. Application Data

(63) Continuation of application No. 13/396,984, filed on Feb. 15, 2012, now Pat. No. 9,151,808.

(30) Foreign Application Priority Data

Feb. 16, 2011 (JP) ................................ 2011-031256
Sep. 8, 2011 (JP) ................................ 2011-195974

(51) Int. Cl.
*G01R 33/032* (2006.01)
*G01R 33/26* (2006.01)
*A61B 5/04* (2006.01)

(52) U.S. Cl.
CPC .......... *G01R 33/032* (2013.01); *G01R 33/26* (2013.01); *A61B 5/04007* (2013.01); *A61B 5/04008* (2013.01); *A61B 2562/0223* (2013.01); *Y10T 29/49982* (2015.01)

(58) Field of Classification Search
CPC . G04F 5/12; G01R 33/032; A61B 2562/0223; A61B 5/04008; A61B 5/04007
See application file for complete search history.

(56) References Cited

U.S. PATENT DOCUMENTS

| | | | |
|---|---|---|---|
| 2,960,197 A | 11/1960 | Langhans | |
| 3,281,709 A * | 10/1966 | Dehmelt | G01N 24/006 324/304 |
| 3,860,311 A | 1/1975 | Shernoff et al. | |
| 4,094,717 A | 6/1978 | Barr | |

(Continued)

FOREIGN PATENT DOCUMENTS

| | | |
|---|---|---|
| CN | 102118165 A | 7/2011 |
| JP | 08-236025 A | 9/1996 |

(Continued)

OTHER PUBLICATIONS

Seltzer et al. "High-temperature alkali vapor cells with antirelaxation surface coatings", 2009, Journal of Applied Physics, vol. 106, Issue 11.

(Continued)

*Primary Examiner* — Melissa Koval
*Assistant Examiner* — Courtney McDonnough
(74) *Attorney, Agent, or Firm* — Harness, Dickey & Pierce, P.L.C.

(57) ABSTRACT

A production method of a gas cell includes: forming a coating layer on a surface of a plate material; assembling a plurality of the plate materials having the coating layer formed thereon so as to form a cell surrounded by the surface having the coating layer formed thereon; and filling the formed cell with an alkali metal gas.

12 Claims, 12 Drawing Sheets

(56) References Cited

U.S. PATENT DOCUMENTS

| | | | |
|---|---|---|---|
| 5,500,302 A | 3/1996 | Phillips et al. | |
| 7,666,485 B2 | 2/2010 | Lal et al. | |
| 8,299,860 B2 | 10/2012 | Youngner et al. | |
| 2005/0184815 A1* | 8/2005 | Lipp | G04F 5/14 331/94.1 |
| 2005/0236460 A1 | 10/2005 | Abbink et al. | |
| 2006/0132130 A1* | 6/2006 | Abbink | G01C 19/60 324/304 |
| 2007/0120563 A1 | 5/2007 | Kawabata et al. | |
| 2008/0093543 A1 | 4/2008 | Hersman | |
| 2010/0159780 A1 | 6/2010 | Hitzschke et al. | |
| 2011/0128082 A1 | 6/2011 | Maki et al. | |
| 2011/0193555 A1 | 8/2011 | Sugioka et al. | |

FOREIGN PATENT DOCUMENTS

| | | |
|---|---|---|
| JP | 11-238469 A | 8/1999 |
| JP | 2007-167616 A | 7/2007 |
| JP | 2009-140984 A | 6/2009 |
| JP | 2009-162554 A | 7/2009 |
| JP | 2009-212416 A | 9/2009 |
| JP | 2009-236599 A | 10/2009 |
| JP | 2010-085134 A | 4/2010 |
| JP | 2010-534918 A | 11/2010 |

OTHER PUBLICATIONS

Grbax Singh, et al. "A Technique for preparing Wall Coated Cesium Vapor Cells", The Review of Scientific Instruments, vol. 43, No. 9 (pp. 1388-1389) (1972).

\* cited by examiner

PRODUCTION METHOD OF GAS CELL, AND GAS CELL

CROSS-REFERENCE TO RELATED APPLICATIONS

This is a continuation patent application of U.S. application Ser. No. 13/396,984, filed Feb. 15, 2012, which claims priority to Japanese Patent Application No. 2011-195974, filed Sep. 8, 2011, and Japanese Patent Application No. 2011-031256, filed Feb. 16, 2011, all of which are incorporated by reference herein in their entireties.

BACKGROUND

1. Technical Field

The present invention relates to a production method of a gas cell, and a gas cell.

2. Related Art

As a biomagnetism measuring apparatus which detects a magnetic field emitted from the heart of a living body or the like, an optical pumping type magnetic sensor has been used. JP-A-2009-236599 discloses a magnetic sensor using a gas cell, pump light, and probe light. In the magnetic sensor, atoms sealed in the gas cell are excited by the pump light and cause spin polarization. Since the polarization plane of the probe light is rotated according to a magnetic field, the magnetic field is measured using the rotation angle of the polarization plane of the probe light.

JP-A-11-238469, U.S. Pat. No. 7,666,485, and "A Technique for preparing Wall Coated Cesium Vapor Cells" in The Review of Scientific Instruments, Vol. 43, No. 9, pp. 1388-1389 (1972) by Grbax Singh, Philip Diavore, and Carrol O. Alley, disclose techniques for filling a cell with a gas.

When a plurality of gas cells are produced, if characteristics of the gas cells vary, this is reflected in the variations of the sensitivity of the magnetic sensor.

SUMMARY

An advantage of some aspects of the invention is that it provides a technique for enhancing uniformity of characteristics of gas cells.

According to an aspect of the invention, there is provided a production method of a gas cell including: forming a coating layer on a first surface of a plate material; assembling a plurality of the plate materials having the coating layer formed thereon so as to form a cell surrounded by the surface having the coating layer formed thereon; and filling the formed cell with alkali metal atoms.

According to the production method, compared to a case where a coating layer is formed after assembly, uniformity of the thickness of the coating layer on the inner wall of the gas cell may be enhanced.

In this aspect, the plate material may have a second surface at the rear of the first surface, in the forming of the coating layer, the coating layer may be formed on the first and second surfaces of the plate material, and in the assembling of the plurality of the plate materials, a plurality of the cells including a first cell surrounded by a plurality of surfaces including the first surface and a second cell surrounded by a plurality of surfaces including the second surface may be formed.

According to the production method, in a cell array having the plurality of the cells, uniformity of the thickness of the coating layer on the inner wall of the gas cell may be enhanced.

In this aspect, the plurality of the cells may have a third cell in which an alkali metal solid is placed, through-holes may be provided in the plate materials between the first and second cells, and the third cell, and the filling of the formed cell with alkali metal atoms may include vaporizing the alkali metal solid in the third cell so as to generate an alkali metal gas, and diffusing the generated alkali metal gas into the first and second cells from the third cell via the through-holes.

According to the production method, compared to a case where an alkali metal gas is individually sealed in each of the cells in the cell array having the plurality of the cells, uniformity of the concentration of the alkali metal gas may be enhanced.

In this aspect, the plurality of the cells may have a fourth cell and a fifth cell, a cell group including the first, second, fourth, and fifth cells may be two-dimensionally disposed on a plane, and the third cell may be positioned on the plane.

According to the production method, the gas cell in which the third cell is two-dimensionally disposed with respect to the cell group may be produced.

In this aspect, the plurality of the cells may have a fourth cell and a fifth cell, a cell group including the first, second, fourth, and fifth cells may be two-dimensionally disposed on a plane, and the third cell may be stacked in a direction perpendicular to the plane with respect to the cell group.

In the production method, the gas cell in which the third cell is three-dimensionally disposed with respect to the cell group may be produced.

In this aspect, the production method may further include cutting the plate material having the coating layer formed thereon into a plurality of plate materials, and in the assembling of the plurality of the plate materials, the plurality of plate materials obtained in the cutting of the plate material may be assembled.

In the production method, the number of plate materials handled in the forming of the coating layer may be reduced, so that compared to the case where the forming of the coating layer is performed after cutting, handling of the plate materials becomes easy.

According to another aspect of the invention, there is provided a gas cell including: an outer wall that forms a closed space; an inner wall that divides the closed space into a plurality of cells; a through-hole that is formed in the inner wall and connects at least one cell from among adjacent cells; and alkali metal atoms sealed in the cells.

According to the gas cell, in a cell array having the plurality of cells, uniformity of the characteristics of the gas cells may be enhanced.

Moreover, according to a further aspect of the invention, there is provided a gas cell including: a wall surface that forms a closed space; and a first ampoule that is accommodated in the closed space and includes an alkali metal therein.

According to a production method of the gas cell, the gas cell may be stably produced without depending on the skill of operating personnel.

In this aspect, the gas cell may have a coating layer that is formed on the wall surface of the closed space and suppresses relaxation of a spin-polarized state of atoms of the alkali metal.

According to the gas cell, the gas cell may be stably produced without depending on the skill of the operating personnel.

In this aspect, the closed space may have a first main chamber filled with the atoms of the alkali metal, an accommodation chamber that accommodates the first ampoule, and a first hole that connects the first main chamber to the accommodation chamber.

According to the gas cell, even in a case where the first ampoule is accommodated in the accommodation chamber, the gas cell is stably produced without depending on the skill of the operating personnel.

In this aspect, the first ampoule may include a buffer gas for suppressing the movement speed of the atoms of the alkali metal.

According to the gas cell, even in a case where the buffer gas is included in the first ampoule, the gas cell may be stably produced without depending on the skill of the operating personnel.

In this aspect, the buffer gas may be a noble gas.

According to the gas cell, even in a case where the noble gas is included in the first ampoule, the gas cell may be stably produced without depending on the skill of the operating personnel.

In this aspect, the first ampoule may have a through-hole for diffusing the buffer gas to the outside of the first ampoule.

According to the gas cell, the buffer gas may be diffused into the closed space.

In this aspect, the closed space may have a second main chamber that is filled with atoms of the alkali metal and is different from the first main chamber, and a second hole that connects the first main chamber to the second main chamber.

According to the gas cell, the cell having a plurality of the main chambers may be stably produced without depending on the skill of the operating personnel.

In this aspect, the first ampoule may have an absorbing material that absorbs light for forming the through-hole.

According to the gas cell, even in a case where the first ampoule is illuminated with light, the gas cell may be stably produced without depending on the skill of the operating personnel.

In this aspect, the gas cell may have a second ampoule that includes therein a coating material for forming the coating layer.

According to the gas cell, even in a case where the second ampoule is accommodated in the accommodation chamber, the gas cell may be stably produced without depending on the function of the operating personnel.

In this aspect, the alkali metal may be a solid or a liquid.

According to the gas cell, even though the alkali metal accommodated in the first ampoule is the solid or the liquid, the gas cell may be stably produced without depending on the skill of the operating personnel.

Moreover, according to a still further aspect of the invention, there is provided a production method of a gas cell including: in a cell having a wall surface that forms a closed space and a first ampoule that is accommodated in the closed space and includes an alkali metal therein, breaking the first ampoule; and diffusing the alkali metal into the closed space after breaking the first ampoule.

According to the production method of a gas cell, the gas cell may be stably produced without depending on the skill of the operating personnel.

In this aspect, the breaking of the first ampoule may include forming a through-hole through light illumination on the first ampoule.

According to the production method of a gas cell, the gas cell may be stably produced using the light illumination.

In this aspect, the light illumination may be performed using a pulse laser that performs light illumination at a pulse width of 1 microsecond or less.

According to the production method of a gas cell, the gas cell may be stably produced using the pulse laser.

In this aspect, the breaking of the first ampoule may include breaking the first ampoule through the light illumination on the first ampoule.

According to the production method of a gas cell, compared to a case where the first ampoule is broken by forming a through-hole using the light illumination, degassing is reduced.

In this aspect, the light illumination may be performed using a pulse laser that performs light illumination at a pulse width of 1 nanosecond or less.

According to the production method of a gas cell, the gas cell may be stably produced using the pulse laser.

In this aspect, the production method of a gas cell may have forming a stress concentration portion in the first ampoule.

According to the production method of a gas cell, compared to a case where the stress concentration portion is not provided, the gas cell may be stably produced.

In this aspect, the breaking of the first ampoule may include adding an acceleration to the cell.

According to the production method of a gas cell, the gas cell may be stably produced using physically adding an acceleration.

In this aspect, the breaking of the first ampoule may include applying heat that generates thermal stress in the first ampoule.

According to the production method of a gas cell, the gas cell may be stably produced using the applying of heat.

BRIEF DESCRIPTION OF THE DRAWINGS

The invention will be described with reference to the accompanying drawings, wherein like numbers reference like elements.

DESCRIPTION OF EXEMPLARY EMBODIMENTS

1. Configuration

Figure 1:
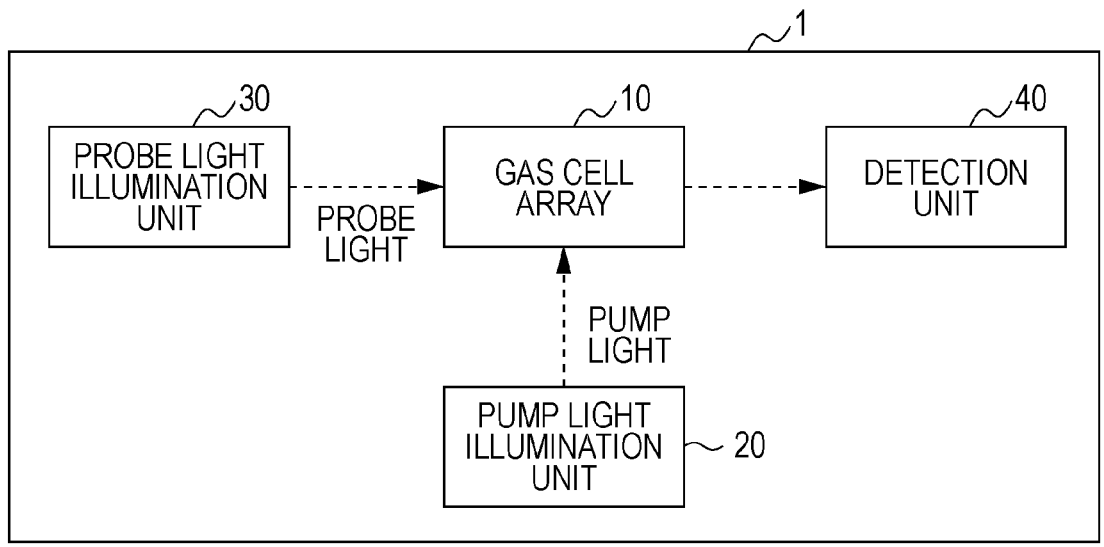
FIG. 1 is a block diagram illustrating the configuration of a magnetic measuring apparatus.

FIG. 1 is a block diagram illustrating the configuration of a magnetic measuring apparatus 1 according to an embodiment. The magnetic measuring apparatus 1 is a living body state measuring apparatus which measures a magnetic field generated from a living body such as a magnetic field generated from a heart (cardiac magnetism) or a magnetic field generated from a brain (cerebral magnetism), as the index of the state of the living body. The magnetic measuring apparatus 1 has a gas cell array 10, a pump light illumination unit 20, a probe light illumination unit 30, and a detection unit 40. The gas cell array 10 has a plurality of gas cells. In the gas cells, an alkali metal gas (for example, cesium (Cs)) is sealed. The pump light illumination unit 20 outputs pump light that interacts with alkali metal atoms (for example, light having a wavelength of 894 nm corresponding to the cesium D1 line). The pump light has a circularly polarized component. When the pump light is illuminated, the outermost electrons of the alkali metal atoms are excited, resulting in spin polarization. The spin-polarized alkali metal atoms undergo precession movement by a magnetic field B where an object to be measured occurs. Spin polarization of a single alkali metal atom is relaxed as time elapses. However, since the pump light is CW (Continuous Wave) light, formation and relaxation of the spin polarization is repeated simultaneously in parallel or continuously. As a result, in view of the group of atoms as a whole, normal spin polarization is formed.

The probe light illumination unit 30 outputs probe light having a linearly polarized component. Before and after transmission of the gas cells, the polarization plane of the probe light is rotated by the Faraday effect. The rotation angle of the polarization plane is the function of a magnetic field B. The detection unit 40 detects the rotation angle of the probe light. The detection unit 40 has an optical detector that outputs a signal corresponding to the amount of incident light, a process that processes the signal, and a memory that stores data. The processor calculates the strength of the magnetic field B using the signal output from the optical detector. The processor writes data representing the calculated result in the memory. In this manner, the user may obtain information of the magnetic field B generated from the object to be measured.

Figure 2:
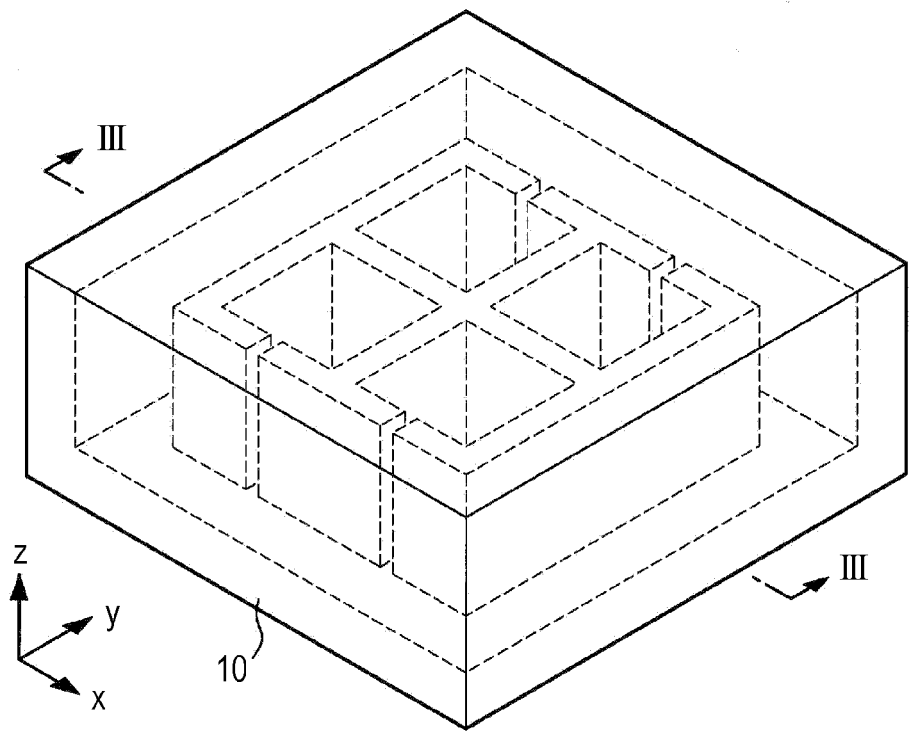
FIG. 2 is an outer appearance diagram of a gas cell array.

FIG. 2 is an outer appearance diagram of the gas cell array 10. In this example, the gas array cell 10 has a plurality of (2×2) gas cells two-dimensionally arranged on the xy plane. The gas cells are cells (boxes) in which an alkali metal gas is sealed. The gas cells are formed using a material having light transmission properties such as quartz glass or borosilicate glass. In addition, the gas cell array 10 has a dummy cell provided to surround the 2×2 gas cells on the xy plane. The 2×2 gas cells at the center are cells that contribute to measurement of the magnetic field, while the dummy cell is a cell that does not contribute to the measurement of the magnetic field.

Figure 3:
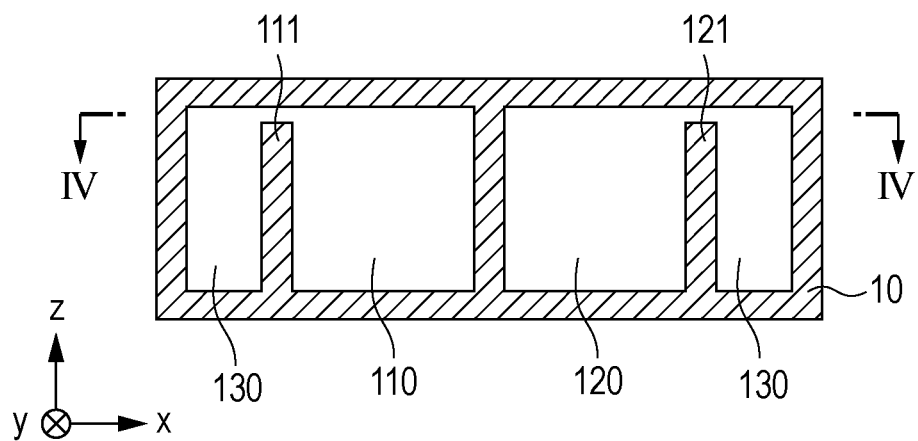
FIG. 3 is a cross-sectional view of the gas cell array taken along the line III-III.

FIG. 3 is a cross-sectional view of the gas cell array 10 taken along the line III-III. This cross-section is parallel to the xz plane. In this cross-section, a gas cell 110, a gas cell 120, and a dummy cell 130 are illustrated. A through-hole 111 is provided between the gas cell 110 and the dummy cell 130. A through-hole 121 is provided between the gas cell 120 and the dummy cell 130.

Figure 4:
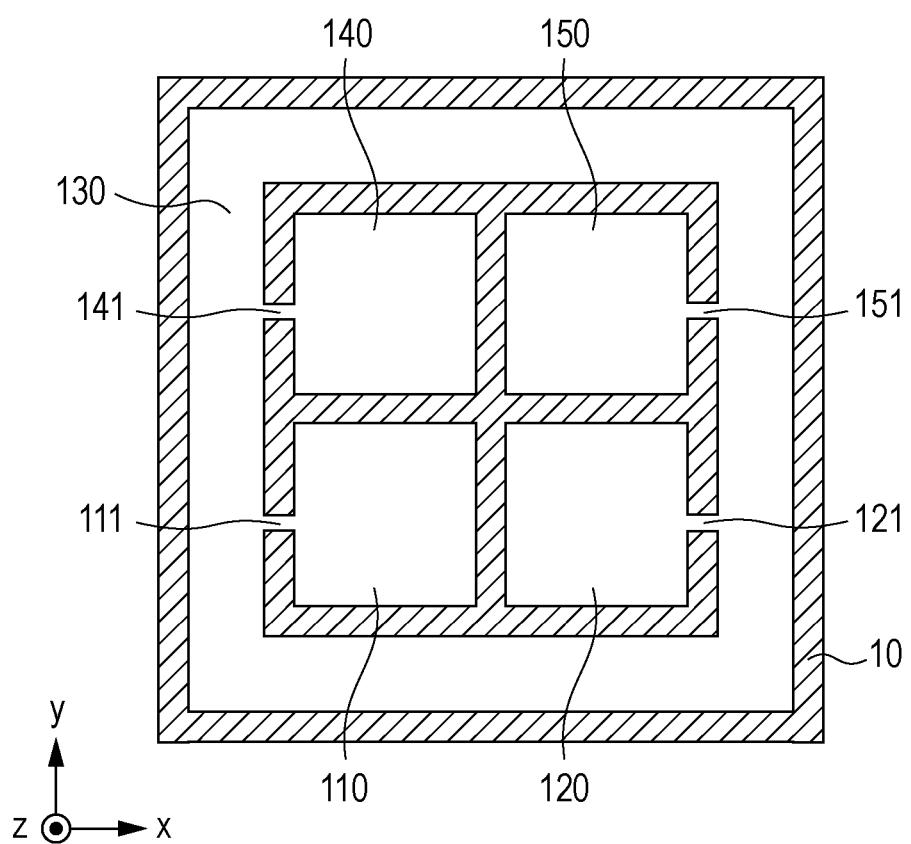
FIG. 4 is a cross-sectional view of the gas cell array taken along the line IV-IV.

FIG. 4 is a cross-sectional view of the gas cell array 10 taken along the line IV-IV. This cross-section is parallel to the xy plane. In this cross-section, the gas cell 110, the gas cell 120, a gas cell 140, a gas cell 150, and the dummy cell 130 are illustrated. A through-hole 141 is provided between the gas cell 140 and the dummy cell 130. A through-hole 151 is provided between the gas cell 150 and the dummy cell 130. The functions of the through-holes 111, 121, 141, and 151 will be described later.

2. Production Method

Figure 5:
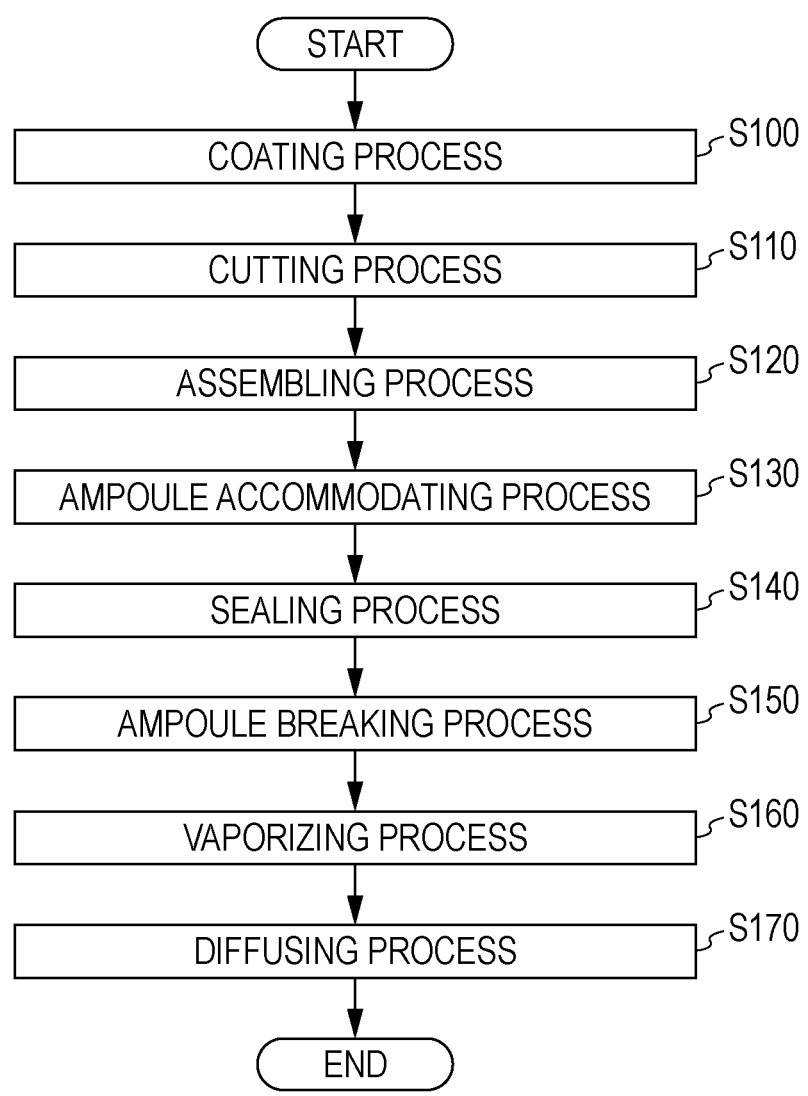
FIG. 5 is a flowchart showing production processes of the gas cell array.

FIG. 5 is a flowchart showing production processes of the gas cell array 10. In Step S100 (coating process), a coating layer is formed on a plate material for forming gas cells. For the coating layer, for example, paraffin is used. The coating layer is applied by a dry process or a wet process. The coating layer is applied to both front and rear surfaces of the plate material.

In Step S110 (cutting process), the plate material having the coating layer formed thereon is cut.

Figure 6:
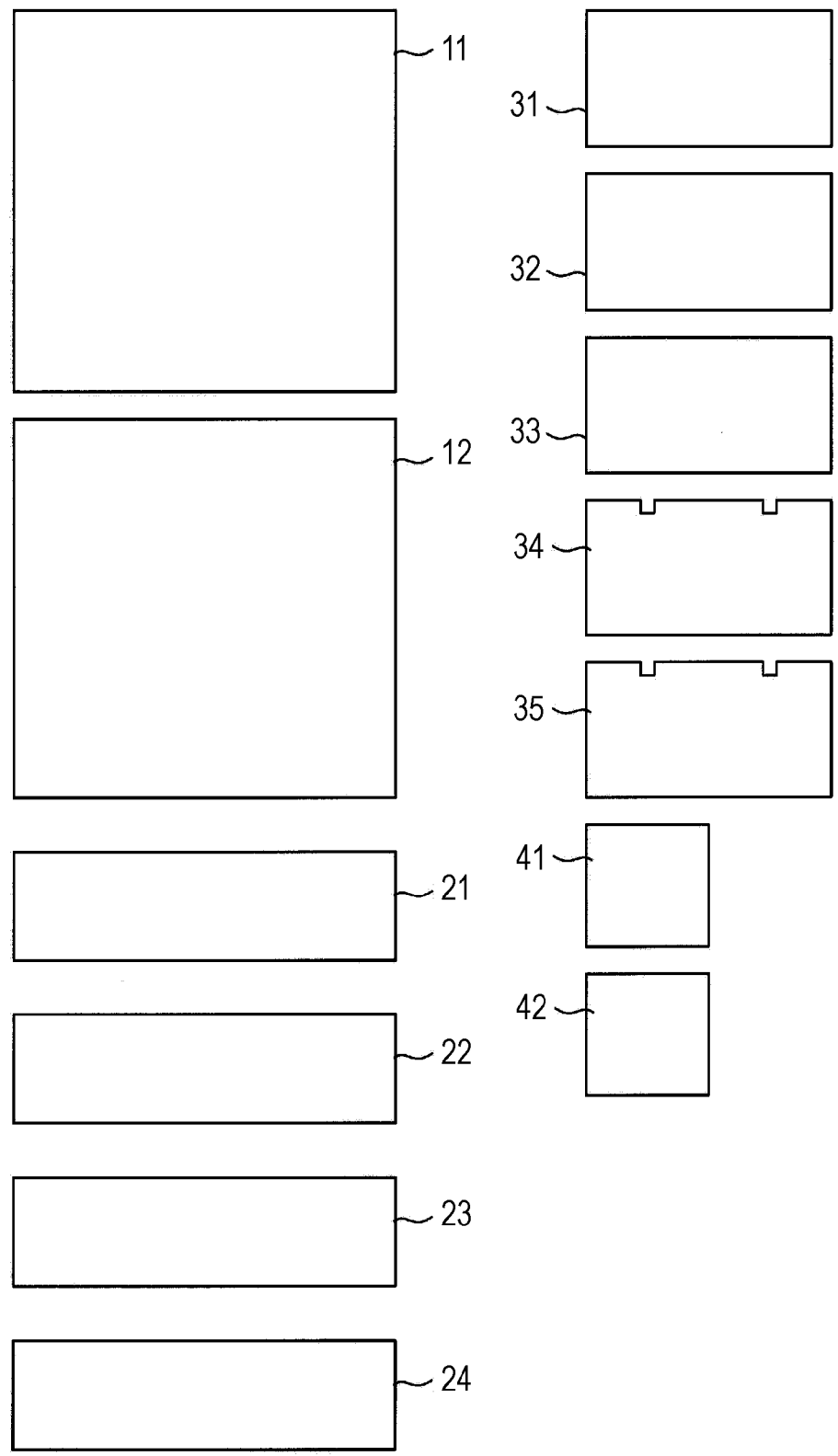
FIG. 6 is a diagram illustrating plate materials which are cut.

FIG. 6 is a diagram illustrating plate materials which are cut. A plate material 11 and a plate material 12 are members that form the upper surface and the lower surface of the gas cell array 10. Here, "upper" means the positive direction in the z axis of FIG. 1, and "lower" means the negative direction in the z axis. A plate material 21, a plate material 22, a plate material 23, and a plate material 24 are members that form the outer side surfaces of the gas cell array 10. The "outer side surfaces" mean surfaces that are perpendicular to the xy plane and are exposed to the outside. A plate material 31, a plate material 32, a plate material 33, a plate material 34, a plate material 35, a plate material 41, and a plate material 42 are members that form the gas cells. The plate material 34 and the plate material 35 are provided with grooves (recessed portions) that are to be through-holes (the through-holes 111, 121, 141, and 151). In this example, the plate materials 31, 32, and 33 form wall surfaces parallel to the xz plane. The plate materials 31, 32, and 33 are sequentially arranged in a direction in which the y axis coordinates are increased. The plate materials 34, 35, 41, and 42 form wall surfaces parallel to the yz plane.

Returning to FIG. 5, in Step S120 (assembling process), the cut plate materials are assembled. In this time point, in order to accommodate an ampoule thereafter, the plate materials are assembled to achieve a state where at least one surface is open. For example, all members except for the plate material 11 that forms the upper surface of the gas cell array 10 are assembled. During assembly, the plate materials are bonded by, for example, fusing or adhesion using an adhesive material.

In Step S130 (ampoule accommodating process), the ampoule is accommodated in the dummy cell 130 in the gas cell array 10. The ampoule is accommodated from the open surface.

Figure 7:
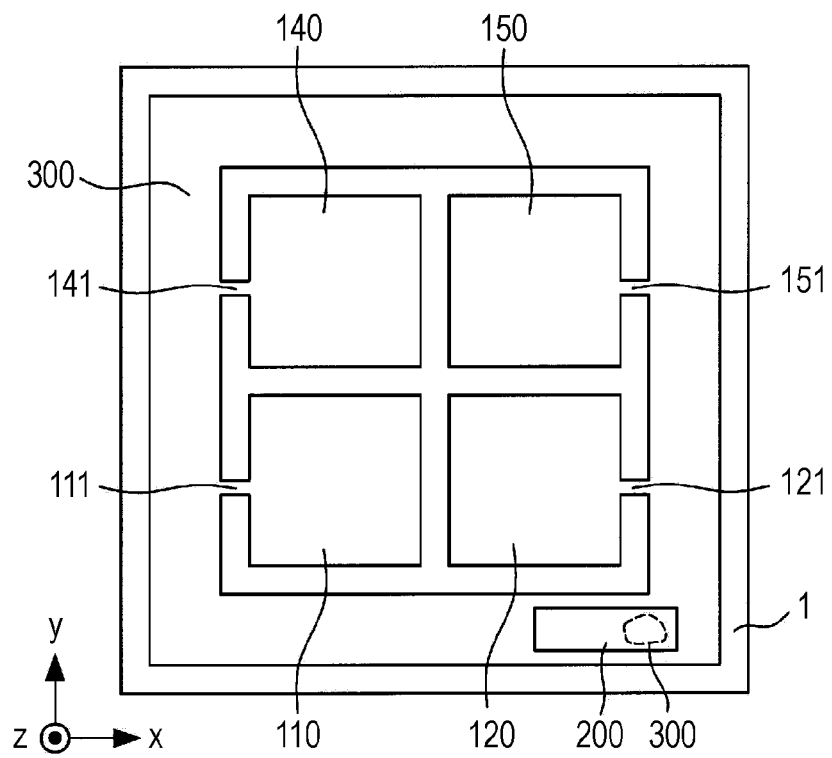
FIG. 7 is a schematic diagram illustrating the gas cell array in which an ampoule is accommodated.

FIG. 7 is a schematic diagram illustrating the gas cell array 10 in which the ampoule is accommodated. FIG. 7 illustrates the same cross-section as that of FIG. 4. An alkali metal solid 300 is sealed in the ampoule 200.

Returning to FIG. 5, in Step S140 (sealing process), the gas cell array 10 is sealed. In this example, in the gas cell, in addition to the alkali metal gas, an inert gas (buffer gas) such as a noble gas is sealed. Therefore, sealing of the gas cell array 10 is performed under an inert gas atmosphere. Specifically, in the inert gas atmosphere, the member (for example, the plate material 11 constituting the upper surface) of the open surface is bonded.

In Step S150 (ampoule breaking process), the ampoule 200 is broken. Specifically, the ampoule 200 is illuminated with laser light focusing on the ampoule 200, such that a hole is open in the ampoule.

In Step S160 (vaporizing process), the alkali metal solid in the ampoule 200 is vaporized. Specifically, the alkali metal solid is heated and vaporized by heating the gas cell array 10.

In Step S170 (diffusing process), the alkali metal gas is diffused. Specifically, by maintaining a certain temperature (preferably a higher temperature than the room temperature) for a predetermined time, the alkali metal gas is diffused.

Figure 8:
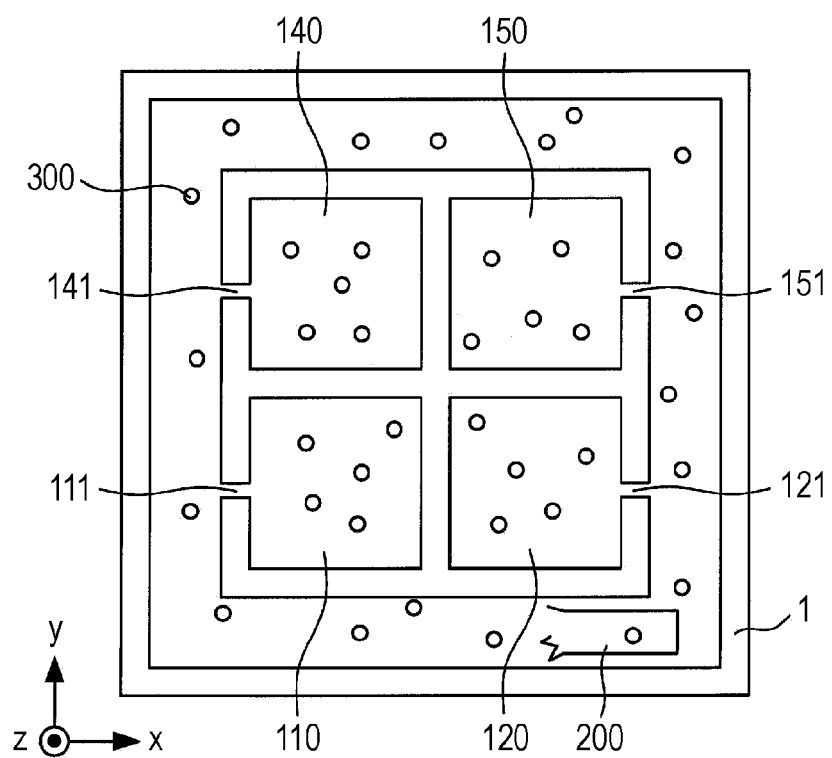
FIG. 8 is a schematic diagram illustrating the gas cell array in which an alkali metal gas is diffused.

FIG. 8 is a schematic diagram illustrating the gas cell array 10 in which an alkali metal gas is diffused. FIG. 8 illustrates the same cross-section as that of FIG. 4. In FIG. 8, white circles schematically represent atoms of the alkali metal gas. In the diffusing process, the alkali metal gas is diffused from the dummy cell 130 to the gas cells 110, 120, 140, and 150 via the through-holes 111, 121, 141, and 151. When a sufficient time for the diffusing process is allowed, the alkali metal gas is diffused to all the gas cells substantially uniformly.

In conclusion, the production processes of the gas cell array 10 include the coating process (Step S100) of forming the coating layer on the surfaces of the plate material, the cutting process (Step S110) of cutting the plate material having the coating layer formed thereon into a plurality of plate materials, the assembling process (Step S120) of assembling the plurality of plate materials having the coating layer formed thereon to form the cells surrounded by the surfaces having the coating layer formed thereon, and a filling process of filling the cells with the alkali metal gas. The plate material has a first surface and a second surface at the rear of the first surface. In the coating process, the coating layer is formed on the first and second surfaces of the plate material. In the assembling process, a plurality of cells are formed which include a first cell (the gas cell 110) surrounded by a plurality of surfaces including the first surface and a second cell (the gas cell 120) surrounded by a plurality of surfaces including the second surface. The gas cell array 10 has a third cell (the dummy cell 130) in which the alkali metal solid is placed. Through-holes are provided in the plate materials between the first and second cells and third cell. The filling process includes the ampoule breaking process (Step S150), the vaporizing process (Step S160), and the diffusing process (Step S170). The alkali metal solid is placed in the third cell in a state of being sealed in the ampoule. A breaking process is a process of breaking the ampoule before the diffusing process. The vaporizing process is a process of generating the alkali metal gas by vaporizing the alkali metal solid in the third cell. The diffusing process is a process of diffusing the generated alkali metal gas from the third cell to the first and second cells via the through-holes.

In addition, the gas cell array 10 has an outer wall that forms a closed space, an inner wall that partitions the closed space into the plurality of cells, through-holes connecting at least one cell of the adjacent cells, and the alkali metal gas sealed in the cell. In addition, the "cell" mentioned here may not be a completely closed space but may be a space connected to other cells via through-holes.

Figure 9:
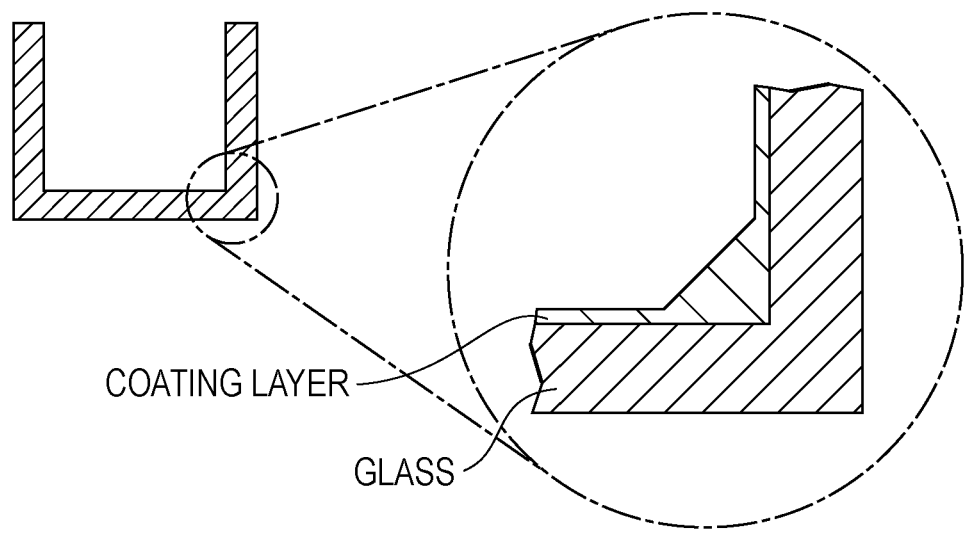
FIG. 9 is a diagram illustrating the configuration of a comparative example.

FIG. 9 is a diagram illustrating the configuration of a comparative example. FIG. 9 illustrates an example in which the coating process is performed subsequently to the assembling process. In this case, the coating layer may be thickly formed at specific places such as corner portions of the cells and boundary portions between the surfaces. As such, if the thickness of the coating layer is non-uniform, when the alkali metal atoms moving in the gas cells collide with the wall surfaces, the movements of the atoms after collision may partially vary to different degrees. This may be the cause of measurement error.

Contrary to this, according to this embodiment, since the coating layer is formed before the assembling process, a more uniform coating layer is formed compared to a case where the coating layer is formed after the assembling process. That is, according to this embodiment, compared to the case where the coating layer is formed after the assembling process, uniformity of the characteristics of the gas cells is enhanced (variations are suppressed).

3. Other Embodiments

The invention is not limited to the embodiments described above, and various modifications can be made. Hereinafter, several modified examples will be described. Two or more of the following modified examples may be combined for use.

3-1. Modified Example 1

Figure 10:
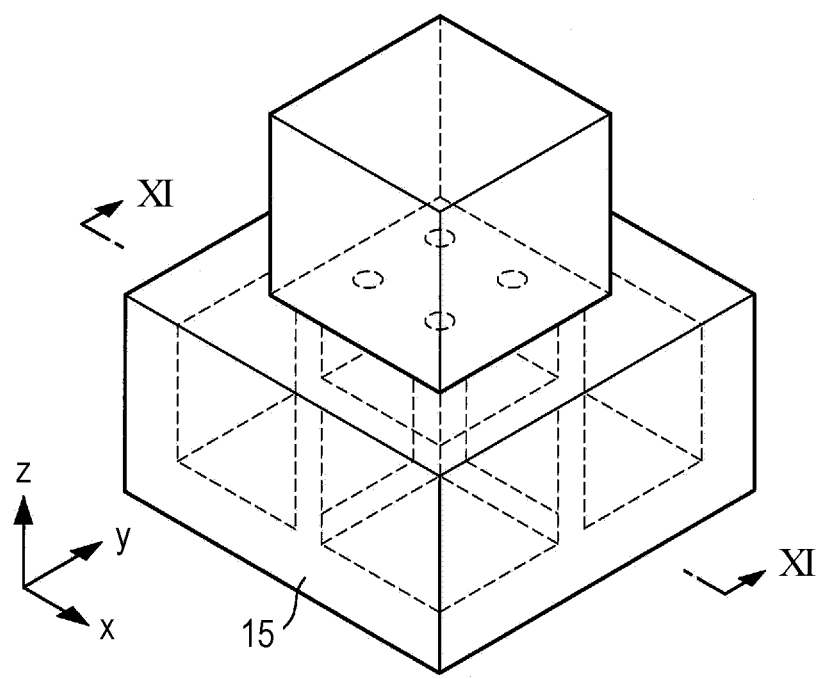
FIG. 10 is an outer appearance diagram of a gas cell array according to Modified Example 1.

FIG. 10 is an outer appearance diagram of a gas cell array 15 according to Modified Example 1. The shape of the gas cell array is not limited to those described in the embodiments. The gas cell array 15 has a dummy cell 160 instead of the dummy cell 130. The dummy cell 160 is different from the dummy cell 130 of the gas cell array 10 in the positional relationship with the gas cell group. In addition, the dummy cell means a cell that does not contribute to the measurement of a magnetic field and a cell for accommodating an ampoule. The gas cell array 10 has the gas cell 110 (an example of the first cell), the gas cell 120 (an example of the second cell), the gas cell 140 (an example of a fourth cell), the gas cell 150 (an example of a fifth cell), and the dummy cell 130 (an example of the third cell). The cell group including the gas cells 110, 120, 140, and 150 are two-dimensionally arranged on the xy plane (arranged in a matrix form). Regarding the cell group, the dummy cell 130 is positioned on the same xy plane as the cell group. Regarding this, in the gas cell array 15, the dummy cell 160 (another example of the third cell) is stacked on the cell group (in the positive direction in the z axis, that is, a direction perpendicular to the plane to which the cell group belongs). According to the gas cell array 15, compared to the gas cell array 10, the size thereof on the xy plane may be reduced. In addition, in a case where light having a component parallel to the xy plane is incident, the attenuation amount of the component of the light parallel to the xy plane is reduced compared to the gas cell array 10 as the light does not pass through the dummy cell.

Figure 11:
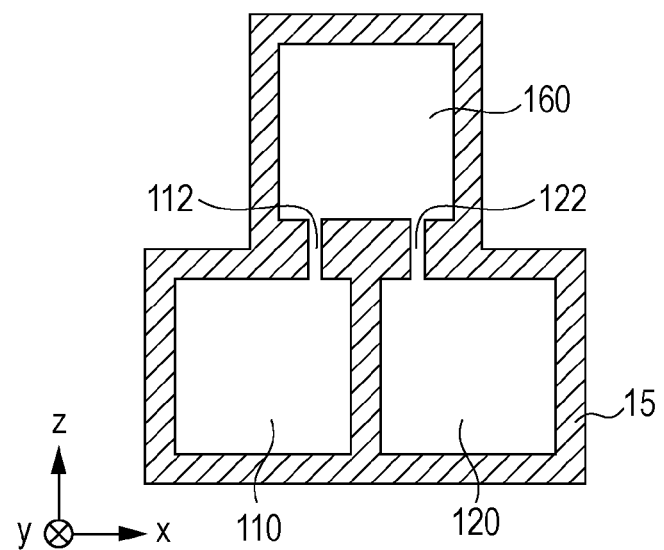
FIG. 11 is a cross-sectional view of the gas cell array taken along the line XI-XI.

FIG. 11 is a cross-sectional view of the gas cell array 15 taken along the line XI-XI. In this example, the gas cells 110 and 120 have through-holes 112 and 122 connected to the dummy cell 160. Although not illustrated in the cross-sectional view, the gas cells 140 and 150 also have through-holes connected to the dummy cell 160.

3-2. Modified Example 2

Figure 12:
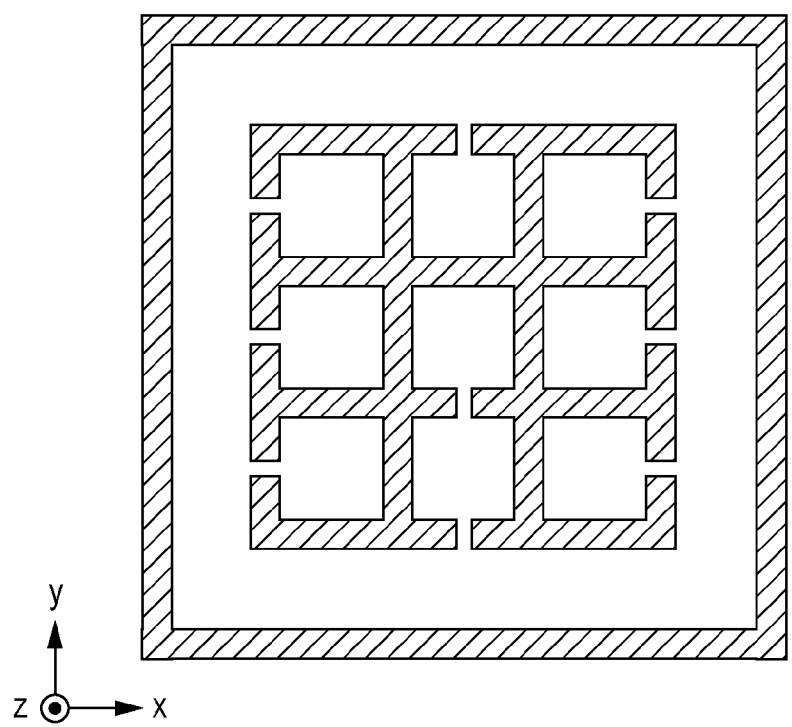
FIG. 12 is a schematic diagram illustrating the arrangement of through-holes according to Modified Example 2.

FIG. 12 is a schematic diagram illustrating the arrangement of through-holes according to Modified Example 2. FIG. 12 illustrates the same cross-section as that of FIG. 4. In the embodiment, an example in which the gas cell array 10 has the gas cells arranged in two rows and two columns is described. However, the number of gas cells is not limited to this. FIG. 12 illustrates a gas cell array having gas cells arranged in three rows and three columns. Like the gas cell array 10, in a configuration in which a dummy cell is disposed in the periphery of the gas cell group on the same plane as the gas cell group, when the number of gas cells is greater than three rows and three columns, a gas cell that is not adjacent to the dummy cell is present. In the example of FIG. 12, the gas cell at the center from among the gas cells in three rows and three columns is not adjacent to the dummy cell. In this case, the gas cell at the center has a through-hole for connection to the other adjacent gas cells. In the diffusing process, the alkali metal gas is diffused via the through-hole and the adjacent other gas cells.

3-3. Modified Example 3

Figure 13:
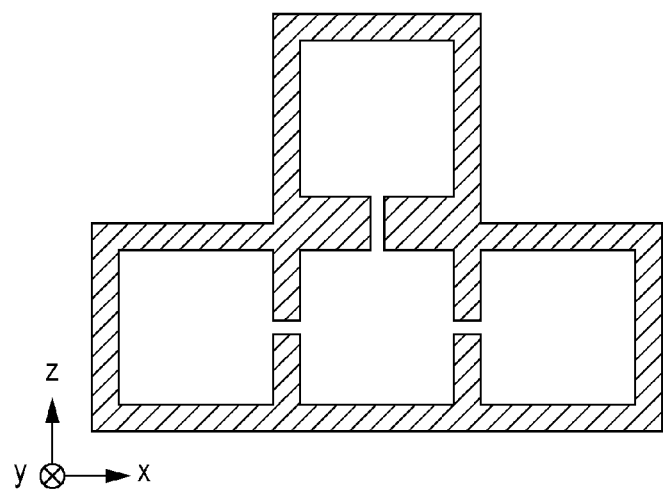
FIG. 13 is a schematic diagram illustrating the arrangement of through-holes according to Modified Example 3.

FIG. 13 is a schematic diagram illustrating the arrangement of through-holes according to Modified Example 3. FIG. 13 illustrates an example in which a dummy cell is stacked in the z direction in a gas cell array having gas cells in three rows and three columns, like Modified Example 1. FIG. 13 illustrates the same cross-section as that of FIG. 10. In this example, from among the gas cells in the three rows and three columns, gas cells other than the gas cell at the center are not adjacent to the dummy cell. In this case, the gas cells other than the gas cell at the center have through-holes for connection to the gas cell at the center. In the diffusing process, the alkali metal gas is diffused via the through-holes and the gas cell at the center.

3-4. Modified Example 4

The specific contents of the ampoule breaking process are not limited to those described in the embodiment. The ampoule 200 may have a part in which two materials that are different in thermal expansion coefficient are adhered. In this case, in the ampoule breaking process, instead of illumination of laser light, (the entire gas cell array accommodating) the ampoule 200 is heated. During heating, due to the difference in thermal expansion coefficient, a degree of heat to break the ampoule 200 is added.

3-5. Modified Example 5

The production method of the gas cell array is not limited to that exemplified in FIG. 5. Other processes may be added to the processes shown in FIG. 5. Otherwise, the order of the processes may be changed, or a part of the processes may be omitted. For example, the sequence of the coating process and the cutting process may be changed. In this case, the plate material is first cut, and after the cutting, the coating layer is formed. For another example, after forming the coating layer, a process of peeling a part thereof may be included. In this case, in the plate material, the coating layer of a part bonded to the other plate material is peeled. Otherwise, in the plate material, the coating layer of a surface exposed to the outside may be peeled.

For another example, the sealing process may be performed in vacuum. In this case, the gas cell does not have an inert gas therein and has only the alkali metal gas.

3-6. Modified Example 6

The shape of the dummy cell is not limited to that described in the embodiment. The dummy cell may have a recessed portion for holding broken pieces of the ampoule. The recessed portion is provided in, for example, a corner part in order to minimize the influence on measurement of a magnetic field. The recessed portion may be formed in the plate material before assembly, and may also be formed by bonding a part that is to be the recessed portion to the plate material having an open hole. In addition, an adhesive material may also be accumulated in the recessed portion so that broken pieces of the ampoule are not moved during movement (transportation).

3-7. Modified Example 7

The shape of the gas cell is not limited to that described in the embodiment. In the embodiment, an example in which the shape of the gas cell is cubic is described. However, the shape of the gas cell may be a polyhedral as well as cubic, or a shape having a curved surface in a part, such as a cylindrical shape. For example, the gas cell may have a reservoir (metal pool) for collecting the alkali metal solid when the temperature is reduced to be equal to or lower than a temperature at which the alkali metal atoms are coagulated. In addition, the alkali metal may be gasified at least during measurement and may not need to be always in a gas state.

3-8. Modified Example 8

Figure 14:
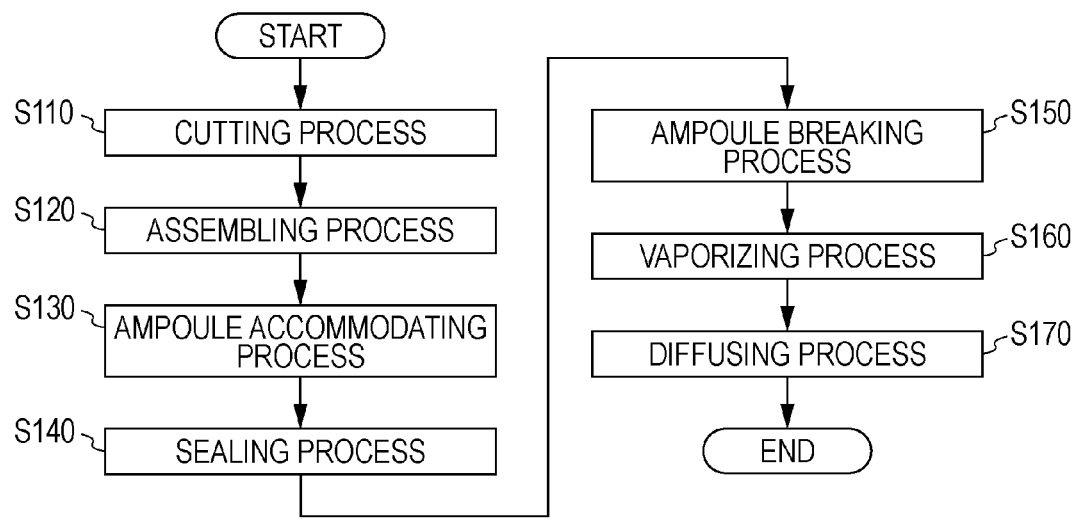
FIG. 14 is a flowchart showing production processes of a gas cell array according to Modified Example 8.

FIG. 14 is a flowchart showing production processes of a gas cell array according to Modified Example 8. In this example, the inner wall of a gas cell does not have a coating layer. Therefore, the flow of FIG. 14 is made by omitting the coating process from the flow of FIG. 5. Even in this case, compared to an example in which the alkali metal solid is accommodated in the cell closed one by one (a cell that is not connected to other cells), the concentration of the alkali metal gas in the cells may be further uniformized. That is, uniformity of the characteristics of the plurality of gas cells may be further enhanced. In addition, the gas cell array has a structure in which a plurality of partition walls are interposed by the two flat plates (the upper and lower surfaces). Using the two flat plates, uniformity of the shapes may be enhanced compared to a case where single gas cells other than in an array form are produced using individual plate materials.

3-9. Modified Example 9

Figure 15:
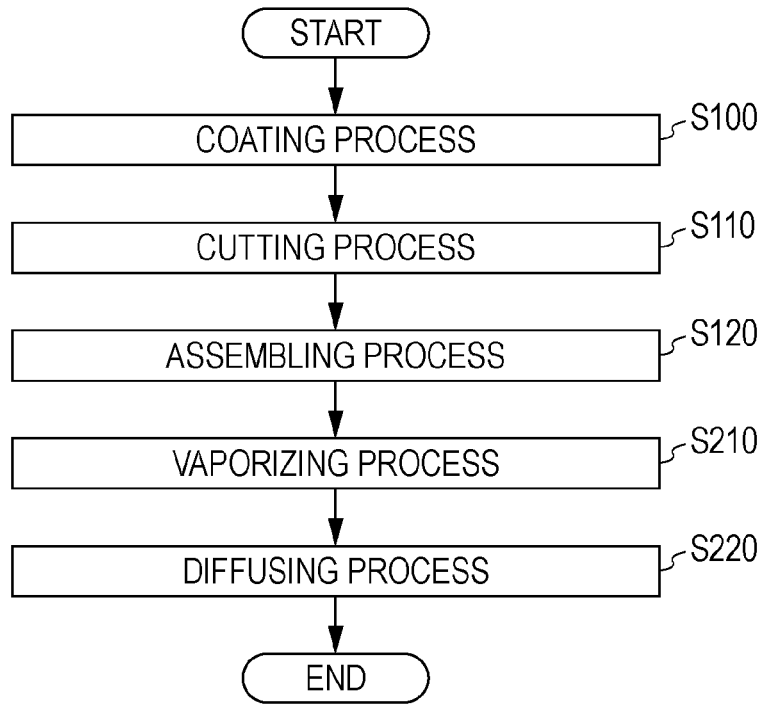
FIG. 15 is a flowchart showing production processes of a gas cell array according to Modified Example 9.

FIG. 15 is a flowchart showing production processes of a gas cell array according to Modified Example 9. In this example, the gas cell array does not have a dummy cell. A part of the gas cell array is connected to a reservoir through a glass tube. A solid of an alkali metal compound is put into the reservoir. In Step S210 (vaporizing process), the reservoir is heated. The alkali metal compound is decomposed by heating the reservoir, and the alkali metal gas is generated. In Step S220 (diffusing process), the alkali metal gas is diffused into the gas cells via the glass tube. The alkali metal gas that reaches the gas cells is diffused into each gas cell via through-holes. After a sufficient time elapses, the glass tube is heated and cut, and the gas cells are sealed. Even in this case, compared to the example in which the alkali metal gas is sealed in the cell closed one by one (a cell that is not connected to other cells), the concentration of the alkali metal gas in the cells may be further uniformized. That is, uniformity of the characteristics of the plurality of gas cells may be further enhanced. In addition, the gas cell array has a structure in which a plurality of partition walls are interposed by the two flat plates (the upper and lower surfaces). Using the two flat plates, uniformity of the shapes may be enhanced compared to the case where single gas cells other than in an array form are produced using individual plate materials. In addition, the coating process may also be omitted from the flow of FIG. 15. In addition, this gas cell array may have a dummy cell.

For further another example, this production method may also be used for producing single gas cells other than a gas cell array. In this case, a dummy cell may not be formed, and the alkali metal solid may be directly (without using ampoule) accommodated in the gas cells.

3-10. Modified Example 10

Figure 16:
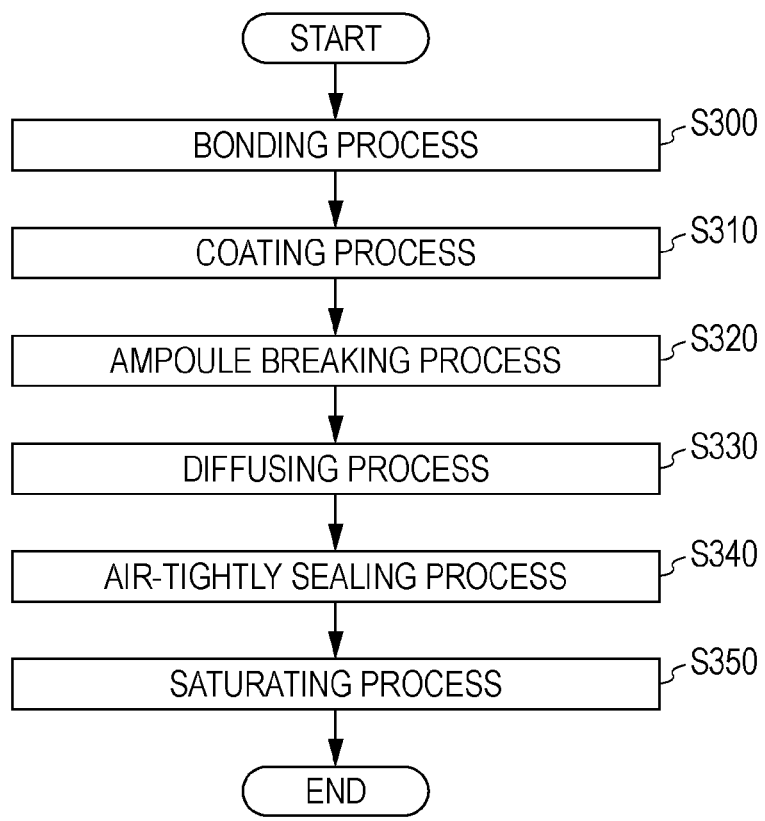
FIG. 16 is a flowchart showing a production method of a gas cell according to Modified Example 10.

FIG. 16 is a flowchart showing a production method of a gas cell according to Modified Example 10. In Step S300 (bonding process), a package and a lid are bonded to each other. The package and the lid are formed of a material that has resistance to alkali metal, such as borosilicate glass or quartz glass.

Figure 17:
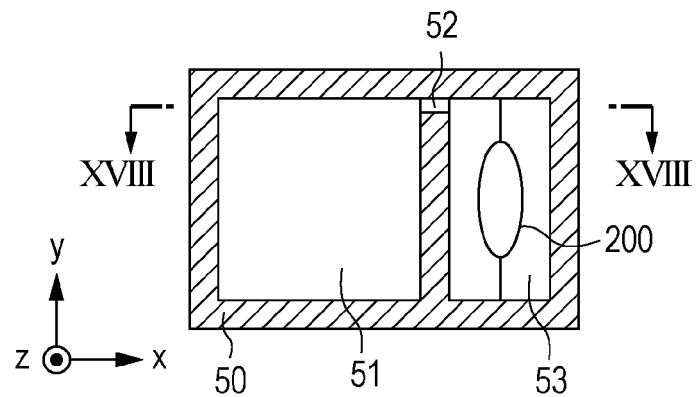
FIG. 17 is a cross-sectional view of a package.

FIG. 17 is a cross-sectional view of the package. FIG. 17 illustrates the cross-section in the xy plane. A package 50 has a main chamber 51, a throttle hole 52, and an ampoule accommodation chamber 53. The main chamber 51 is a space filled with a gas. The ampoule accommodation chamber 53 is a space that accommodates the ampoule 200. The throttle hole 52 is a hole for connection (communication) between the main chamber 51 and the ampoule accommodation chamber 53. The coating layer described in the embodiment has an effect in suppressing relaxation of the spin-polarized state. However, when the throttle hole 52 is increased in diameter, the effect in non-relaxation by the coating layer is damaged. On the contrary, when the throttle hole 52 is reduced in diameter, it takes time to cause a coating agent described later to flow in. Therefore, the diameter of the throttle hole 52 is designed in consideration of the balance of the two. That is, this cell has wall surfaces that form a closed space therein. In addition, here, illustration of the alkali metal solid in the ampoule is omitted.

Figure 18:
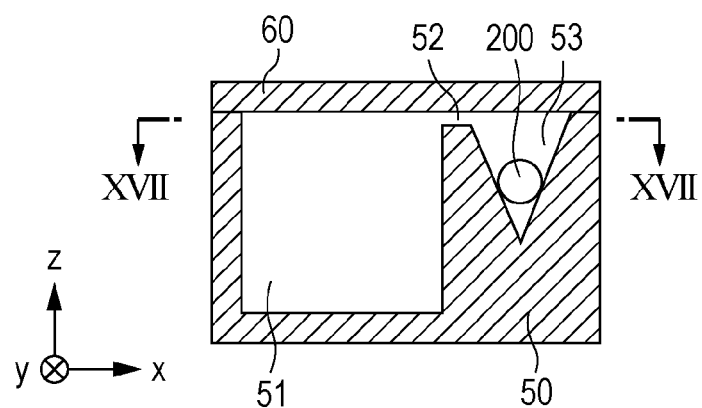
FIG. 18 is a cross-sectional view of a package and a lid.

FIG. 18 is a cross-sectional view of the package and the lid. FIG. 18 illustrates the cross-section in the xz plane (FIG. 17 illustrates the cross-section taken along the line of XVII-XVII of FIG. 18). A lid 60 is a lid that seals the main chamber 51, the throttle hole 52, and the ampoule accommodation chamber 53 of the package 50. The ampoule accommodation chamber 53 has a size and a shape to a degree that makes it accommodate the ampoule 200. In this example, the ampoule accommodation chamber 53 has a V shape (wedge shape) in cross-section. The package 50 and the lid 60 are bonded to each other by bonding using a low-melting-point glass or optical bonding. Bonding between the package 50 and the lid 60 is performed in a state where the entire system is in vacuum (decompressed atmosphere) using a vacuum pump or the like.

Returning to FIG. 16, in Step S310 (coating process), coating is performed. That is, the coating layer is formed on the inner wall of the main chamber 51. The coating layer is formed of hydrocarbon such as paraffin or an organic silicon compound such as OTS (octadecyltrichlorosilane). Such a coating material is caused to flow into the main chamber 51 via a flow passage (not shown) in a liquid or gas state. A plurality of the flow passages may be provided depending on the configuration of the production apparatus and the like.

In Step S320 (ampoule breaking process), the ampoule 200 is broken. Breaking of the ampoule 200 is performed in a vacuum environment. Breaking of the ampoule is performed using, for example, laser light. In this case, the laser light illuminates the ampoule 200 to focus thereon through the lid. In the ampoule 200, a hole is open at a position illuminated with the laser light. In order to enhance absorbance of the laser light, a film of a light absorbing material may be formed on the ampoule 200. For another example, an ultrashort pulse laser (a laser that emits light having a pulse width of 1 nanosecond or less, such as a picosecond laser or femtosecond laser) may be used. In addition, the ampoule 200 may include therein a buffer gas (for example, a noble gas) for suppressing the movement speed of atoms of the alkali metal, in addition to the alkali metal.

Figure 19:
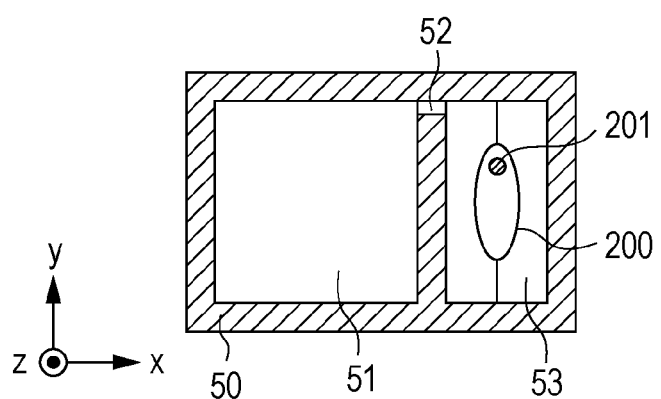
FIG. 19 is a diagram for exemplifying a state after an ampoule is broken.

FIG. 19 is a diagram for exemplifying a state after the ampoule 200 is broken. By illumination of the laser light, in the ampoule 200, a through-hole 201 is open. In the case where the ampoule 200 includes the buffer gas therein, the buffer gas is diffused to the outside of the ampoule 200 via the through-hole 201.

Returning to FIG. 16, in Step S330 (diffusing process), the alkali metal is diffused. By maintaining the cell at a certain temperature (preferably a higher temperature than the room temperature) for a predetermined time, the alkali metal gas is diffused.

In Step S340 (air-tightly sealing process), the cell is air-tightly sealed. Air-tight sealing is performed in a vacuum environment. Air-tight sealing means sealing of the flow passage of the coating material. Air-tight sealing is performed using a sealing material such as a solder or a low-melting-point glass. Otherwise, air-tight sealing may be performed by dissolving glass itself that constitutes the cells (the package 50 and the lid 60). For heating of the sealing material or heating of the cells, lasers may be used.

In Step S350 (saturating process), the alkali metal gas is caused to be absorbed into the coating layer until a saturated state. When the number of alkali metal atoms in the cells is reduced (that is, the density of the alkali metal atoms in the cells is reduced), there may be cases where the measurement results are affected. Here, the cells may be heated. For example, the cells are held for 10 hours in a state of being heated at 85° C.

For example, in the technique of "A Technique for preparing Wall Coated Cesium Vapor Cells" in The Review of Scientific Instruments, Vol. 43, No. 9, pp. 1388-1389 (1972) by Grbax Singh, Philip Diavore, and Carrol O. Alley, operating personnel need to have a skillful glasswork technique, so that there is a problem in that the technique is not appropriate for stable industrial production. However, according to the production method of Modified Example 10, the glass cells may be stably produced without depending on the skill of the operating personnel. Moreover, in the technique of "A Technique for preparing Wall Coated Cesium Vapor Cells" in The Review of Scientific Instruments, Vol. 43, No. 9, pp. 1388-1389 (1972) by Grbax Singh, Philip Diavore, and Carrol O. Alley, a pipe for introducing an alkali metal to cells needs to be bonded to the cells, and thus there may be cases where production of small cells is difficult due to the balance with the size of the pipe. However, according to the production method of Modified Example 10, small cells may also be produced.

3-11. Modified Example 11

Figure 20:
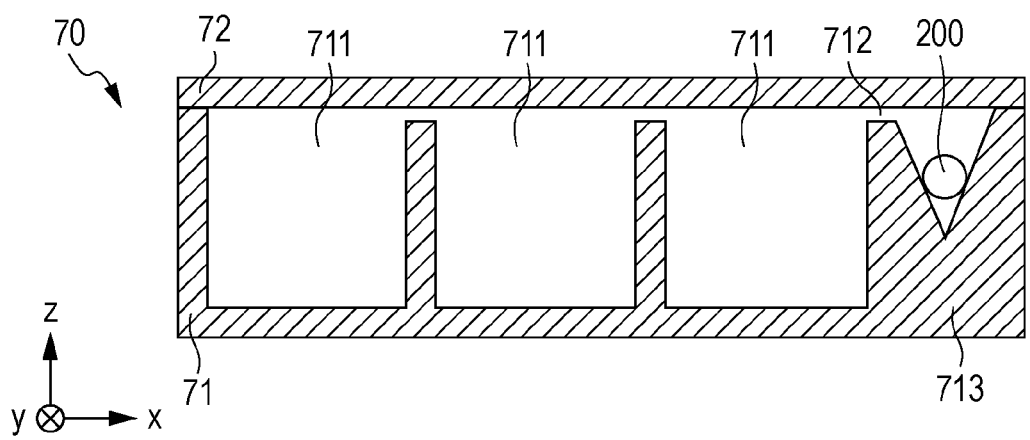
FIG. 20 is a cross-sectional view of a gas cell array according to Modified Example 11.

FIG. 20 is a cross-sectional view of a gas cell array 70 according to Modified Example 11. FIG. 20 illustrates the cross-section in the xz plane. In Modified Example 10, the example in which single cells are produced is described. However, using the method of Modified Example 10, a cell array having a plurality of cells may be formed. The gas cell array 70 has a package 71 and a lid 72. The package 71 has a plurality of main chambers 711, throttle holes 712, and an ampoule accommodation chamber 713. The two neighboring main chambers 711 are connected by the throttle hole 712. The ampoule accommodation chamber 713 and the neighboring main chamber 711 are connected by the throttle hole 712. In addition, in FIG. 20, an example in which only the single ampoule accommodation chamber 713 is provided is illustrated. However, a plurality of ampoule accommodation chambers 713 may also be provided. The production method is common to that of Modified Example 10 except for the shapes of the package and the lid.

3-12. Modified Example 12

Figure 21:
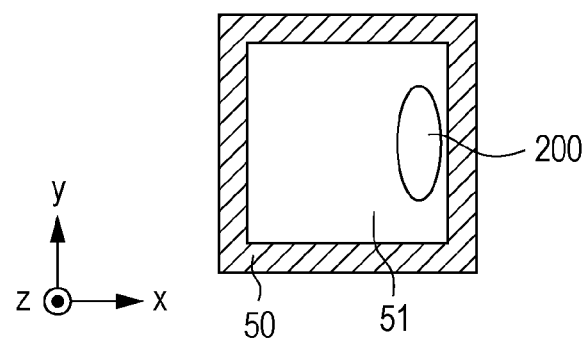
FIG. 21 is a cross-sectional view of a gas cell according to Modified Example 12.

FIG. 21 is a cross-sectional view of a gas cell according to Modified Example 12. FIG. 21 illustrates the cross-section in the xy plane. The gas cell of Modified Example 12 does not have an ampoule accommodation chamber, unlike the gas cell of Modified Example 10. This gas cell has the main chamber 51. The ampoule 200 is accommodated in the main chamber 51. The production method is common to that of Modified Example 10 except for the shapes of the package and the lid.

3-13. Modified Example 13

Figure 22:
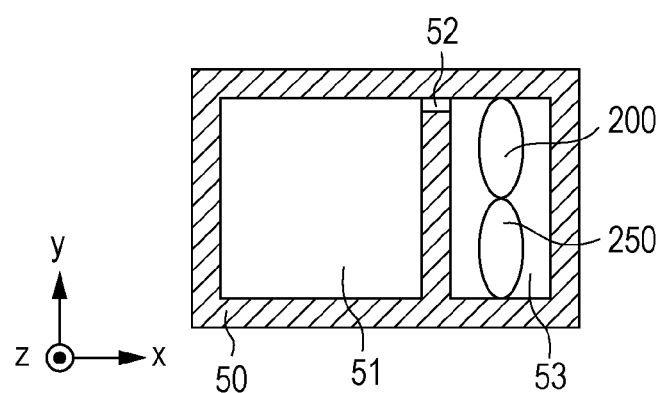
FIG. 22 is a cross-sectional view of a gas cell according to Modified Example 13.

FIG. 22 is a cross-sectional view of a gas cell according to Modified Example 13. This gas cell has the main chamber 51, the throttle hole 52, and the ampoule accommodation chamber 53. In the ampoule accommodation chamber 53, the ampoule 200 and an ampoule 250 are accommodated. The ampoule 250 is an ampoule in which the coating material is sealed. In this example, the ampoule 250 is broken in the coating process. Breaking of the ampoule 250 is performed like the case of the ampoule 200. Other points are the same as those of Modified Example 10.

3-14. Modified Example 14

Breaking of the ampoule is not limited to by illumination of the laser light. The ampoule may be broken by causing the ampoule 200 to collide with the inner wall of the ampoule accommodation chamber 53 by applying physical impacts or vibrations. For another example, heat that generates thermal stress to the ampoule 200 the ampoule 200 may be broken by applying the thermal stress.

3-15. Modified Example 15

Figure 23:
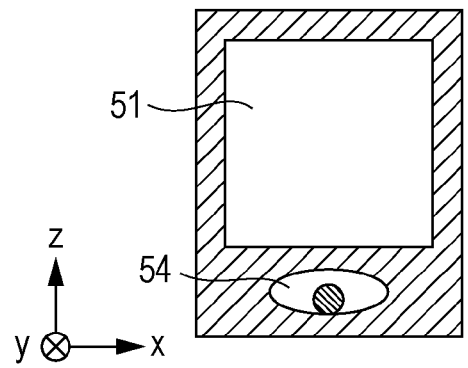
FIG. 23 is a cross-sectional view of a gas cell according to Modified Example 15.

FIG. 23 is a cross-sectional view of a gas cell according to Modified Example 15. FIG. 23 illustrates the cross-section in the xz plane. This gas cell has the main chamber 51 and an alkali metal accommodation chamber 54. In Modified Example 15, the ampoule 200 is not used. The alkali metal accommodation chamber 54 is a space (chamber) provided in the package 50. This space is closed at a time point of production of the gas cells. In the alkali metal accommodation chamber 54, the alkali metal solid is placed.

Figure 24:
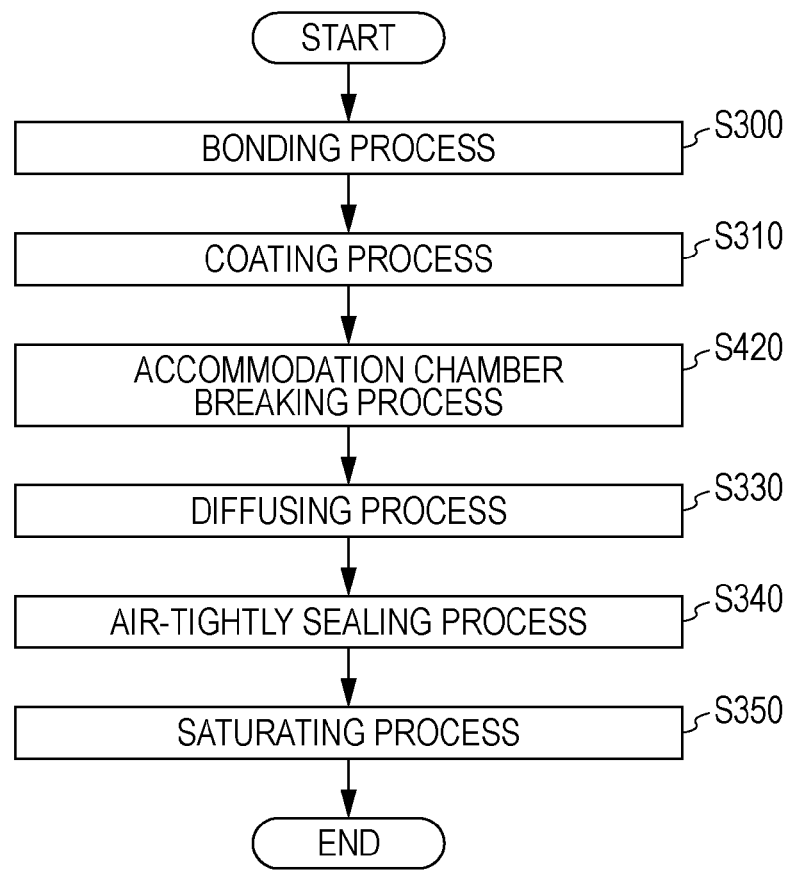
FIG. 24 is a flowchart showing a production method of a gas cell according to Modified Example 15.

FIG. 24 is a flowchart showing a production method of a gas cell according to Modified Example 15. In Step S300 (bonding process), a package and a lid are bonded to each other. In Step S310 (coating process), coating is performed. In Step S420 (accommodation chamber breaking process), the alkali metal accommodation chamber 54, more specifically, the wall surfaces between the main chamber 51 and the alkali metal accommodation chamber 54 are broken. Breaking of the alkali metal accommodation chamber 54 is performed by, for example, illumination of the laser light, like breaking of the ampoule 200. In Step S330 (diffusing process), the alkali metal is diffused. In Step S340 (airtightly sealing process), the cells are air-tightly sealed. In Step S350 (saturating process), the alkali metal gas is caused to be absorbed into the coating layer until a saturated state. In addition, in this example, a coating material accommodation chamber for accommodating the coating material may be provided in the package. In this case, in the coating process, the coating material accommodation chamber is broken.

3-16. Modified Example 16

Instead of through-hole formation by illumination of the laser light, a process of generating thermal stress through light illumination thereby breaking the ampoule 200 by the thermal stress may also be used. According to this method, compared to the case where the through-holes are formed by light illumination, degassing (gas released from glass or the like during the process) is reduced, so that there may be cases where characteristics of a sensor are enhanced. In this case, a laser having a pulse width of nanoseconds or less may be used. Moreover, in order to easily break the ampoule 200, a stress concentration section (for example, a dent) may be formed in the ampoule 200.

In the embodiments and the modified examples described above, an example in which alkali metal atoms mainly in a gas state are introduced to the gas cells. However, the state of the alkali metal atoms introduced to the gas cells is not limited to the gas state. Alkali metal atoms in any of solid, liquid, and gas states may be introduced to the gas cells. In addition, a capsule may also be used instead of the ampoule.

What is claimed is:
1. A magnetic measuring apparatus comprising:
   a pump light that emits a pump light to a gas cell array so that alkali metal atoms in the gas cell array interact;
   a probe light that emits a probe light to the gas cell array, the probe light having a linearly polarized component, a polarized plane of the probe light being rotated by a magnetic field;
   a light detector that detects a rotation angle of the probe light; and
   a processor that is configured to determine the magnetic field based on the detected rotation angle,
   wherein the gas cell array includes:
     an outer wall that forms a closed space;
     an inner wall that divides the closed space into a first cell, a second cell, a third cell, and a fourth cell, the inner wall having a coating layer thereon;

a fifth cell that is provided laterally between the outer wall and a first cell group of the first, second, third, and fourth cells; and first, second, third, and fourth through-holes that are respectively provided between the fifth cell and the first through fourth cells so as to establish gas communication passages therebetween.

2. A magnetic measuring apparatus according to claim 1, wherein a second cell group including the first through fifth cells is two dimensionally arranged on a plane.

3. A magnetic measuring apparatus according to claim 1, further comprising, an ampoule that is arranged in the fifth cell, the ampoule storing the alkali metal atoms therein.

4. The magnetic measuring apparatus according to claim 1, wherein the coating layer includes hydrocarbon.

5. The magnetic measuring apparatus according to claim 4, wherein the hydrocarbon is paraffin.

6. The magnetic measuring apparatus according to claim 1, wherein the coating layer includes organic silicone compounds.

7. The magnetic measuring apparatus according to claim 1, wherein the fifth cell completely surrounds the first through fourth cells in a plan view.

8. The magnetic measuring apparatus according to claim 2, wherein the fifth cell completely surrounds the first through fourth cells in a plan view.

9. The magnetic measuring apparatus according to claim 3, wherein the fifth cell completely surrounds the first through fourth cells in a plan view.

10. The magnetic measuring apparatus according to claim 4, wherein the fifth cell completely surrounds the first through fourth cells in a plan view.

11. The magnetic measuring apparatus according to claim 5, wherein the fifth cell completely surrounds the first through fourth cells in a plan view.

12. The magnetic measuring apparatus according to claim 6, wherein the fifth cell completely surrounds the first through fourth cells in a plan view.

* * * * *